(12) United States Patent
Krachman

(10) Patent No.: US 8,144,948 B2
(45) Date of Patent: Mar. 27, 2012

(54) METHOD AND APPARATUS FOR TRANSPORTING IMAGES

(75) Inventor: Evan Krachman, Shrewsbury, NJ (US)

(73) Assignees: Sony Corporation, Tokyo (JP); Sony Electronics Inc., Park Ridge, NJ (US)

( * ) Notice: Subject to any disclaimer, the term of this patent is extended or adjusted under 35 U.S.C. 154(b) by 1376 days.

(21) Appl. No.: 11/730,205

(22) Filed: Mar. 30, 2007

(65) Prior Publication Data

US 2008/0242946 A1 Oct. 2, 2008

(51) Int. Cl.
*G06K 9/00* (2006.01)
(52) U.S. Cl. ......................... 382/128; 713/168
(58) Field of Classification Search ................. 382/128; 713/168; 714/41
See application file for complete search history.

(56) References Cited

U.S. PATENT DOCUMENTS

| | | | | |
|---|---|---|---|---|
| 5,740,801 A * | 4/1998 | Branson | | 600/407 |
| 6,961,541 B2 * | 11/2005 | Overy et al. | | 455/41.2 |
| 7,124,442 B2 * | 10/2006 | Nash-Putnam | | 726/26 |
| 7,146,025 B2 * | 12/2006 | Cho et al. | | 382/115 |
| 7,278,084 B2 * | 10/2007 | Palin et al. | | 714/758 |
| 7,761,092 B2 * | 7/2010 | Desch et al. | | 455/422.1 |
| 7,848,703 B1 * | 12/2010 | Beard et al. | | 455/41.2 |
| 7,849,309 B1 * | 12/2010 | Brown | | 713/162 |
| 2003/0097351 A1 * | 5/2003 | Rothschild et al. | | 707/1 |
| 2003/0159141 A1 | 8/2003 | Zacharias | | |
| 2005/0001024 A1 * | 1/2005 | Kusaka et al. | | 235/375 |
| 2005/0202844 A1 | 9/2005 | Jabri et al. | | |
| 2005/0265267 A1 | 12/2005 | Hwang | | |
| 2006/0007478 A1 | 1/2006 | Ryu et al. | | |
| 2006/0067295 A1 * | 3/2006 | Lehotsky et al. | | 370/351 |
| 2006/0171363 A1 | 8/2006 | Xavier et al. | | |

* cited by examiner

*Primary Examiner* — Hadi Akhavannik
(74) *Attorney, Agent, or Firm* — Rader, Fishman & Grauer PLLC

(57) ABSTRACT

A portable image transport device and corresponding techniques for image transport are disclosed. The portable image transport device accommodates an automatic initiation of image transport when the device is in a designated location by automatically recognizing the location condition and then engaging in communication with a medical device having an image capture capability. A variety of image transport may be performed, such as sending the received image to a printer for printing a hard copy. The portable image transport device also manages restrictions on image transport. Various restrictions may apply including but not limited to the type of devices to which the transport may be made, or certain registered devices to ensure transport only within a defined set of recipient classes or particularly identified recipients.

16 Claims, 7 Drawing Sheets

METHOD AND APPARATUS FOR TRANSPORTING IMAGES

BACKGROUND OF THE INVENTION

1. Field of the Invention

This invention relates generally to medical image devices and more particularly to methods and apparatus for transporting medical images.

2. Description of the Related Art

The use of digital imagery has become relatively prolific in the medical industry, for original imagery as well as for post-image-acquisition processes, wherein images are distributed or shared to further medical treatment and for other reasons.

Typically, medical service providers use stand alone systems that are configured to communicate with corresponding dedicated devices. These types of systems are inflexible and cannot communicate with a variety of devices. Where addition of a new device is even available as a potential option, alterations to the stand alone system are typically very costly and time consuming, rendering the opportunity for change relatively unavailable.

Additionally, the systems typically use a relatively large workstation with tethered corresponding peripheral devices. This limits the usefulness of the peripheral devices and unduly consumes working space where such space is at a premium.

The implementation of mobile imaging devices that could be used to store and share imagery from surgical or other medical procedures without requiring a tethered connection to a computer has been proposed, but a completely viable solution has not been developed for a number of reasons.

One problem is that there are a number of different medical devices, including stationary scanning devices, devices that are used within the body, and others, and these different medical devices are provided by a variety of manufacturers.

Another problem is the potential for unauthorized image capture and/or distribution. Medical information is highly sensitive and subject to significant privacy constraints, so the capture and distribution of such information should be subject to restrictions that prevent unauthorized parties from capturing images, or receiving captured images that are otherwise authorized but which need to be subject to restrictions on distribution.

There remains a need for a portable medical image device that is convenient while also accommodating interoperability with a variety of devices and that facilitates restrictions on the distribution of medical image content where necessary.

SUMMARY OF THE INVENTION

The present invention provides a portable image transport device and corresponding techniques for image transport.

According to one embodiment, the portable image transport device accommodates an automatic initiation of image transport when the device is in a designated location by automatically engaging in communication with a medical device having an image capture capability to further an image transport. This may comprise receiving an indication that the device is present at a designated location, such as by location determination or by a signal that uniquely identifies a location. Upon such an indication the device initiates a communication with a medical device having an image capture capability. The medical device may be verified as registered for transporting images through the device. An image is then received from the medical device, and transported to another device.

A variety of image transport may be performed, such as sending the received image to a printer for printing a hard copy. There, confirmation of successful printing may be returned to the image transport device using the wireless connection while the device remains at the designated location. This allows the surgeon or other operator to be free to review and print images without having to physically interface with other devices and without having to verify that printing has been successful, freeing time and attention for other activities.

According to another aspect, the portable image transport device manages restrictions on image transport. This may comprise communicating with a medical device having an image capture capability using a wireless connection between the image transport device and the medical device, and verifying that the medical device is registered for transporting images through the image transport device. The medical device is also correlated to image parameters that may indicate a variety of information, such as the format and content of the images, as well as recipient classification information that restricts transport of the images from the registered medical device. The image transport device is then allowed to receive images from the medical device, and transport the received images subject to the identified transport restrictions.

In one example, the hospital or other service provider may manage information related to medical devices, with an association of any given medical device to any given patient at a given time being ascertained and retained. It is thus ascertainable that the medical device at a given time is associated with a particular patient. The image transport parameters incorporate identification of the patient in association with the recipient classification information to restrict distribution or other transport of the images accordingly. Various restrictions may apply including but not limited to the type of devices to which the transport may be made, certain registered devices to ensure transport only within a defined set of recipient classes or particularly identified recipients, or the like.

The present invention can be embodied in various forms, including business processes, computer implemented methods, computer program products, computer systems and networks, user interfaces, application programming interfaces, and the like.

BRIEF DESCRIPTION OF THE DRAWINGS

These and other more detailed and specific features of the present invention are more fully disclosed in the following specification, reference being had to the accompanying drawings, in which.

DETAILED DESCRIPTION OF THE INVENTION

In the following description, for purposes of explanation, numerous details are set forth, such as flowcharts and system configurations, in order to provide an understanding of one or more embodiments of the present invention. However, it is and will be apparent to one skilled in the art that these specific details are not required in order to practice the present invention.

Figure 1A:
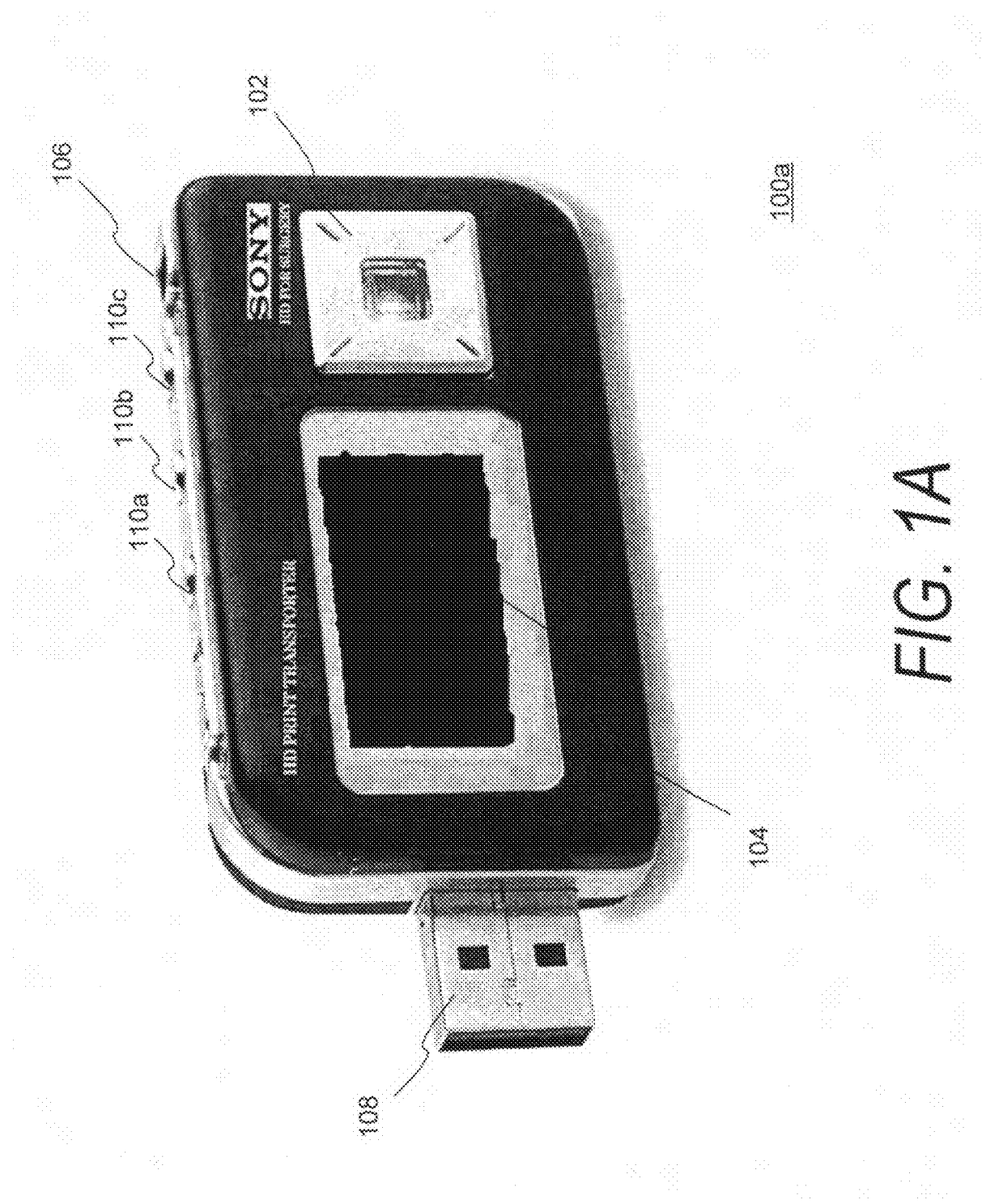
FIG. 1A is a schematic diagram illustrating an embodiment of a portable surgical imaging device.

FIG. 1A is a schematic diagram illustrating an embodiment of a portable medical imaging device 100a. The portable medical imaging device (PMID) 100a enables surgeons or other medical service providers to print, view or share captured digital still or moving images from surgical or other types of medical procedures, and does so in a fashion that allows the provider to work without requiring physical connection to a computer or other device.

The PMID 100a includes a small display area 104 that enables users to view images right on the device without the need to connect to a computer. A variety of display technologies are well known for this purpose, including but not limited to LCD and OLED displays.

The device also includes a viewfinder 102 and a button 106 for engaging in a conventional image capture, as well as input buttons 110a-c that may be configured to accommodate a variety of functions, preferably in correspondence with a user interface that is provided through the display area 104. The user interface may, for example, be icon based with certain buttons providing cursor navigation and certain other buttons accommodating selection of highlighted items.

The PMID 100 also may utilize a wireless connection between various devices, including the digital image capture units of medical devices, printers, a workstation in a local area of interest (e.g., operating room), or another PMID. Connections to these various devices may also involve an existing network, with the wireless connection established between a network router and the PMID 100a. As an alternative, a USB interface 108 accommodates a connection to other equipment via a USB port.

The PMID 100a may store images using industry standard JPEG or MPEG or uncompressed file formats. Preferably, the PMID 100a is configured to accommodate the presentation and transport of images in high definition formats suitable for medical imaging. A graphical user interface accommodates quick selection to share, print or store images. According to one aspect, the PMID 100a is set to automatically receive images from registered devices, and to automatically initiate the receipt of information when the PMID 100a is brought into a local area of interest, such as an operating room.

According to another aspect, the PMID 100a is configured to act as a "gatekeeper" for governing the capture and distribution of medical information, by maintaining or otherwise accessing the registration of medical devices as well as other information useful for identifying a restriction.

The PMID 100a also provides numerous useful features, such as the ability to apply an audio annotation to an image through a built-in microphone (not shown in FIG. 1), or through a headset configured to communicate with the portable medical imaging device 100 such as through a Blue Tooth connection. An example of an audio annotation is where a user speaks the annotation for a given image. The image with the audio annotation may then be shared in various ways as described herein, with the annotation being a useful mechanism for the sender to flag the significance or provide some other associated context for the sent image. In one example, a physician may easily add the audio annotation to a medical image as part of the medical record for that image.

A sharing functionality allows the sender to broadcast an image to a group of colleagues or other recipients, subject to any restrictions on distribution or other transport (if applicable) for a current image. In addition, images may be date/time stamped and have a unique digital watermark to enhance the security of the image and to allow subsequent authentication of the image.

The PMID 100a may be configured for integration with a variety of PC based medical systems, including those provided with ultrasound or other medical image capturing systems.

Figure 1B:
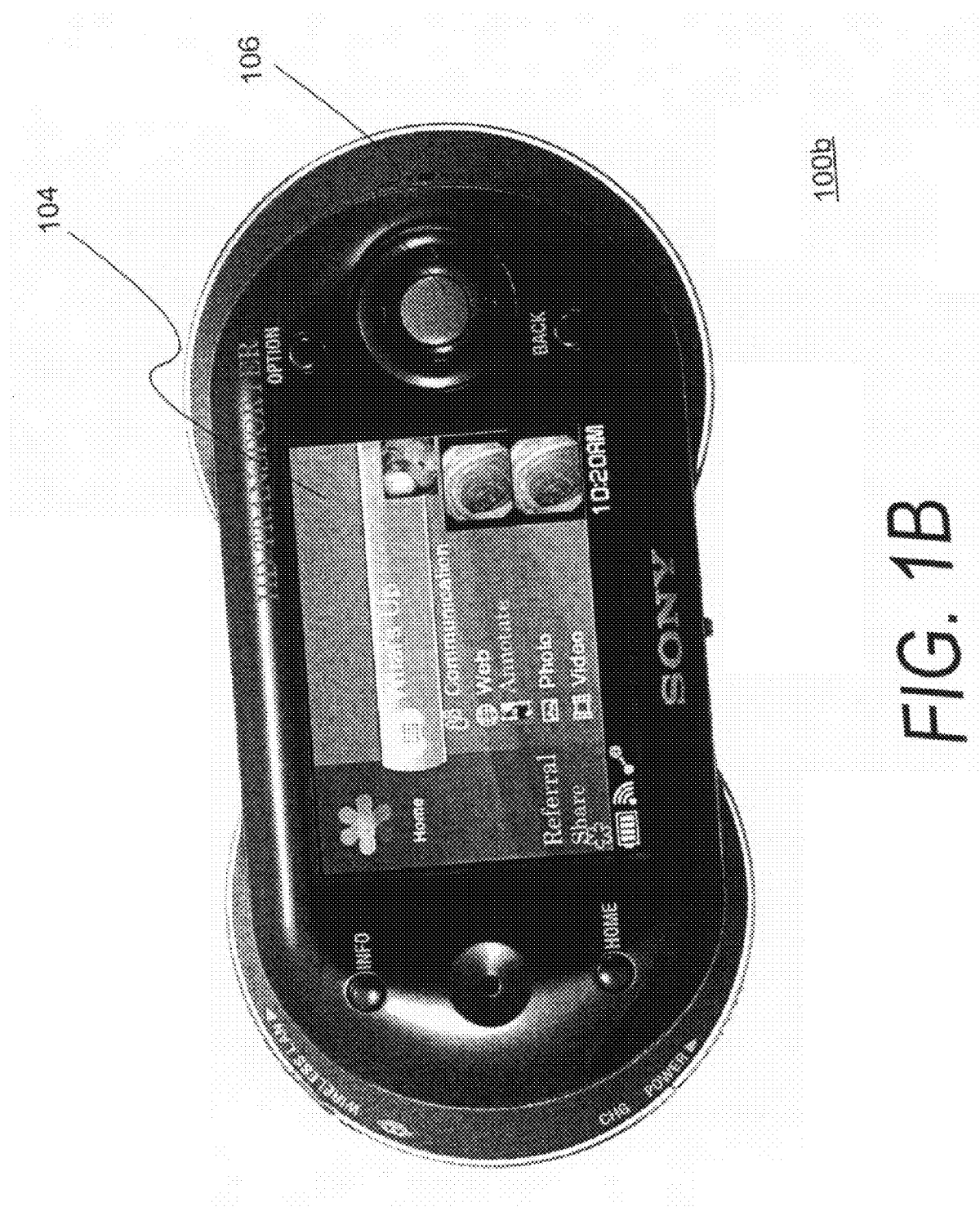
FIG. 1B is a schematic diagram illustrating another embodiment of a portable surgical imaging device.

The PMID may be provided in a variety of different form factors and execution platforms. FIG. 1B is a schematic diagram illustrating another embodiment of a PMID 100b, wherein the form factor differs from that illustrated in FIG. 1A. The PMID 100b also includes and a button for engaging in a conventional image capture and other operations (106), as well as input buttons configurable to accommodate a variety of functions, and the corresponding display area 104. This embodiment may implement the form factor and execution platform provided by the MYLO™ personal communication device as provided by Sony Corporation, Tokyo, Japan. In this embodiment, the PMID 100b is preferably configured to implement a graphical user interface that provides icon based selection of tasks. The PMID 100b may also include a keyboard the slides out for text entry. Annotation of images is accommodated through such text entry or by a microphone for audio annotation.

Figure 2:
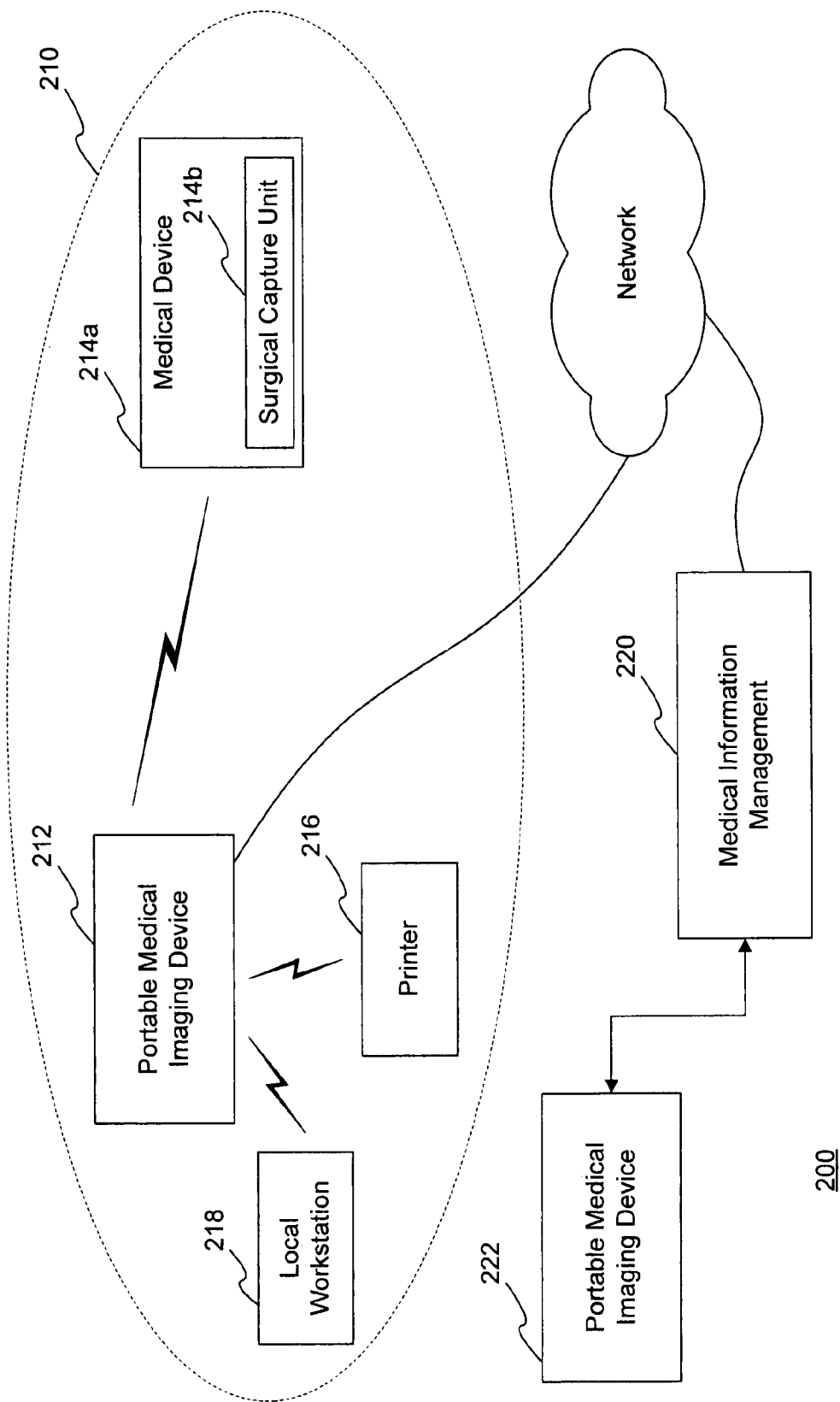
FIG. 2 is a schematic diagram illustrating an environment in which a portable surgical image device may operate.

FIG. 2 is a schematic diagram illustrating an example of an environment 200 in which a portable medical imaging device (PMID) 212 operates. The PMID 212 may operate in a local area of interest 210 such as an operating room, a room where dedicated medical scanning equipment may be used (e.g., ultrasound, MRI, etc.), a room where a medical discussions are conducted, etc. The PMID 212 preferably engages in a wireless connection to other devices to both receive and send images. For example, a medical device 214a may be used in an operating room during a variety of procedures. The user may directly capture an image using the PMID 212 because of its provided image capturing capabilities, or the user may have the PMID 212 communicate with the medical device 214a to obtain an image captured from its image capture unit 214b.

The PMID 212 also engages in wireless communication with other devices to exchange images and potentially other information useful for managing the transport of such images. Examples of these devices are a workstation 218 and a printer 216 resident in the local area of interest. The printer 216 may be used to request an immediate hard copy of an image that has been captured (by the PMID or another device) and possibly reviewed by the user through the PMID 212 display screen. As described further below, the PMID may use wireless LAN or various other wireless communications technologies and protocols in order to engage in wireless communication with other devices.

The PMID 212 also facilities communications with devices outside the local area of interest 201, which may be accommodated using a wired or wireless connection, using conventional network communications or the like. For example, a wireless LAN connection may be made to a hub that in turn accommodates connection through the hospital LAN to connect with a medical information management 220 computer system. The medical information management 220 system may exchange information with the PMID 212, or may facilitate further connection to other devices including one or more other PMIDs 222, printers, displays in conference rooms, workstations, etc. Alternatively, the connection to these devices may be made directly without requiring the medial information management system 220 to intermediate.

There are still other alternatives. For example, the PMID 212 may use a wireless communication to communicate with devices outside the local area of interest 210, without requiring the PMID 212 to use the local area network or the like. In one embodiment, the PMID 212 also functions as a cellular telephone. In that example, the medical images may be transported wirelessly using conventional cellular communication techniques.

Also, in one embodiment the PMID 212 includes location determination technology such as GPS that allows the PMID 212 to monitor its location and to provide functions that are dictated or initiated by location.

Figure 3:
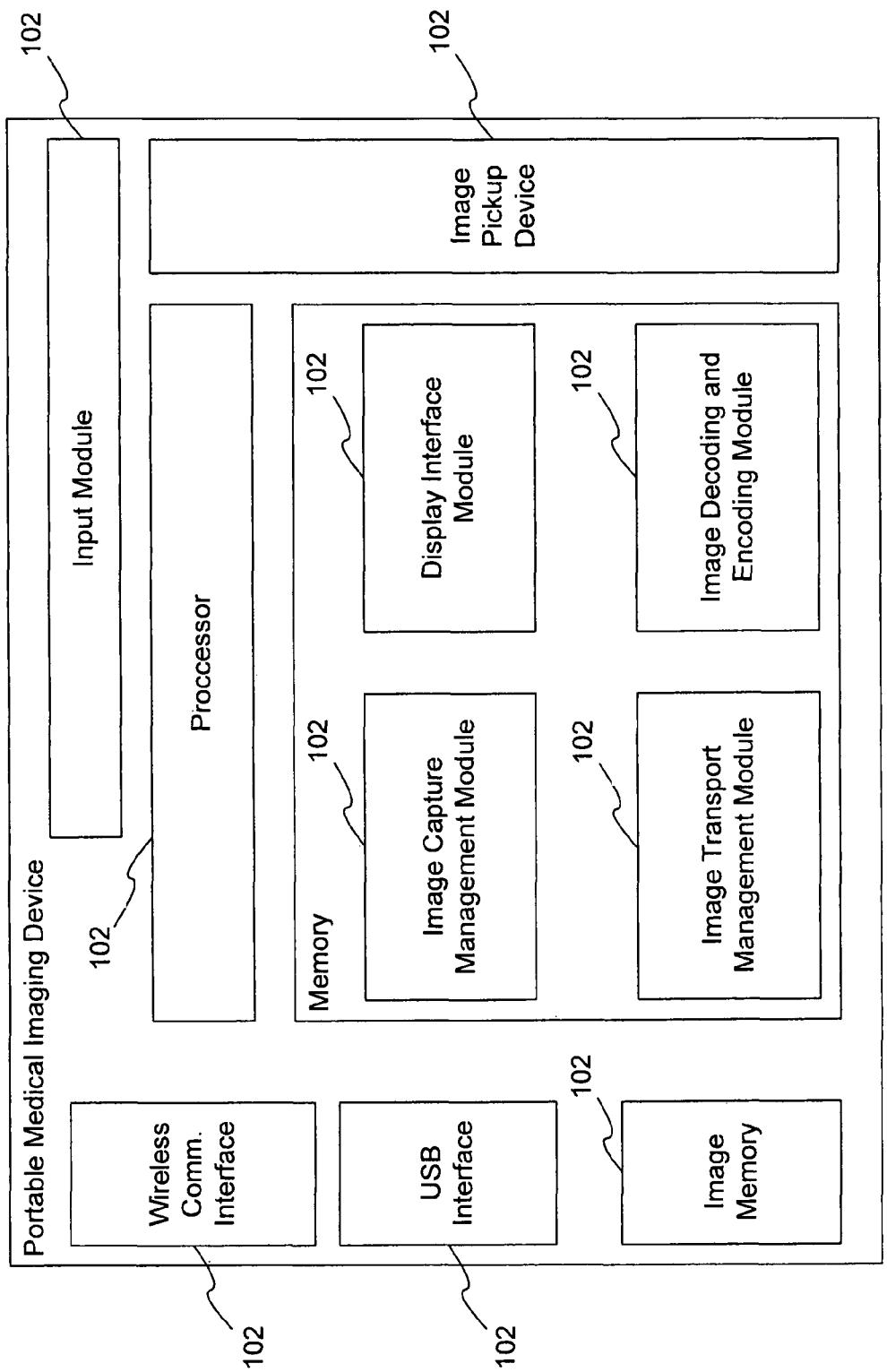
FIG. 3 is a block diagram illustrating an embodiment of a portable surgical imaging device in more detail.

FIG. 3 is a block diagram illustrating an embodiment of a PMID 300 in more detail. The PMID 300 includes an image pickup device 314 that works in conjunction with an input module 312, processor 302 and instructions stored in memory 304 to function as a digital image capture device. The input module 312 provides controls, preferably button types that allow various functional categories as described herein. One functional category is that of a digital camera. There, the controls allow the user to configure the characteristics of image capture, manage the review and disposition of images, and initiate image capture. This functionality is similar to the functionality provided by a standalone digital camera. The image is captured using the image pickup device 314, which is preferably a CCD array that is used to capture images and facilitate pixel representation of the same in the form of a digital file, which in turn may be in raw format, compressed format such as JPEG and/or MPEG, or others.

The PMID 300 also includes an image memory 306, USB interface 308 and wireless communication interface 310. The wireless communication interface 310 accommodates wireless communication between the PMID 300 and other devices. In one embodiment the wireless communication interface 310 is a WLAN network interface, such as one adherent to one or more of the 802.11 family of standards, including implementations referred to as Wi-Fi. The wireless communication interface 310 may also implement other wireless communication standards and techniques, such as the type used for short range communication directly with other devices (e.g., Bluetooth). Finally, various conventional protocols may be used to accommodate communication through the wireless connection, dependent upon the connection type and the type of network over which the communication is made.

The USB interface 308 provides another alternative communication, such as where the interfacing device does not have the capability of communicating with the PMID 300 through the described wireless connection(s). There, the PMID 300 may be interfaced using the USB port of the corresponding device and may communicate with that device accordingly, to engage in the transport of images or the like.

The PMID 300 also includes additional image memory 306, which may be a dedicated memory or may be an interface for receiving a flash memory card on which images are stored.

Some or all of the PMID 300 functionality may be software-based, with the functions being carried out by processor 302 execution of the instructions stored therein. An image decoding and encoding module 322 accommodates the encoding of raw digital images to compressed formats as noted, and may also decode previously encoded images to provide them in raw format, both of which are useful where such a format is desired in connection with image transport. The display interface module 318 provides a graphical user interface through the previously described display, through which the user may review and manage images and their transport using the control buttons. The image capture management module 316 interfaces with the controls and the image pickup device 314 or corresponding buffers to receive digital image information, and also allows the user to generally manage currently and previously captured images for retention, disposal, etc.

Finally, the image transport management module 320 operates to provide image transport functionality, in conjunction with the other elements of the PMID 300. The image transport management module 320 is preferably software but may alternatively be hardware or firmware, or various combinations thereof.

According to one aspect, the image transport management module 320 accommodates an automatic initiation of image transport when the PMID 300 is in a designated location by automatically recognizing the location condition and then engaging in communication with a medical device having an image capture capability to further an image transport. The may comprise receiving an indication that the PMID 300 is present at a designated location, and upon such an indication initiating a communication with a medical device having an image capture capability. In conjunction with this the medical device is verified as registered for transporting images through the PMID 300. Once this is done, the PMID 300 receives an image from the medical device, and transports the received image to another device.

A variety of image transporting may be performed, such as sending the received image to a printer for printing a hard copy. There, confirmation of successful printing may be returned to the PMID 300 using the wireless connection while the PMID 300 remains at the designated location. This allows the surgeon or other operator to be free to review and print images without having to physically interface with other devices and without having to verify that printing has been successful, freeing time and attention for other activities.

According to another aspect, the image transport management module 320 manages restrictions on image transport. This may comprise communicating with a medical device having an image capture capability using the wireless connection between the PMID 300 and the medical device, and verifying that the medical device is registered for transporting images through the PMID 300. The medical device is also correlated to image parameters that may indicate a variety of information, such as the format and content of the images, as well as recipient classification information that restricts transport of the images from the registered medical device. The PMID 300 is allowed to receive images from the medical device, and transport the received images subject to the identified transport restrictions.

In one example, the hospital or other service provider manages information related to medical devices, with an association of any given medical device to any given patient at a given time being ascertained and retained. It is thus ascertainable that the medical device at a given time is associated with a particular patient. The image transport parameters incorporate identification of the patient in association with the recipient classification information to restrict distribution or other transport of the images accordingly. Various restrictions may apply including but not limited to the type of devices to which the transport may be made, certain registered devices to ensure transport only within a define set of recipient classes or particularly identified recipients, or the like.

Figure 4:
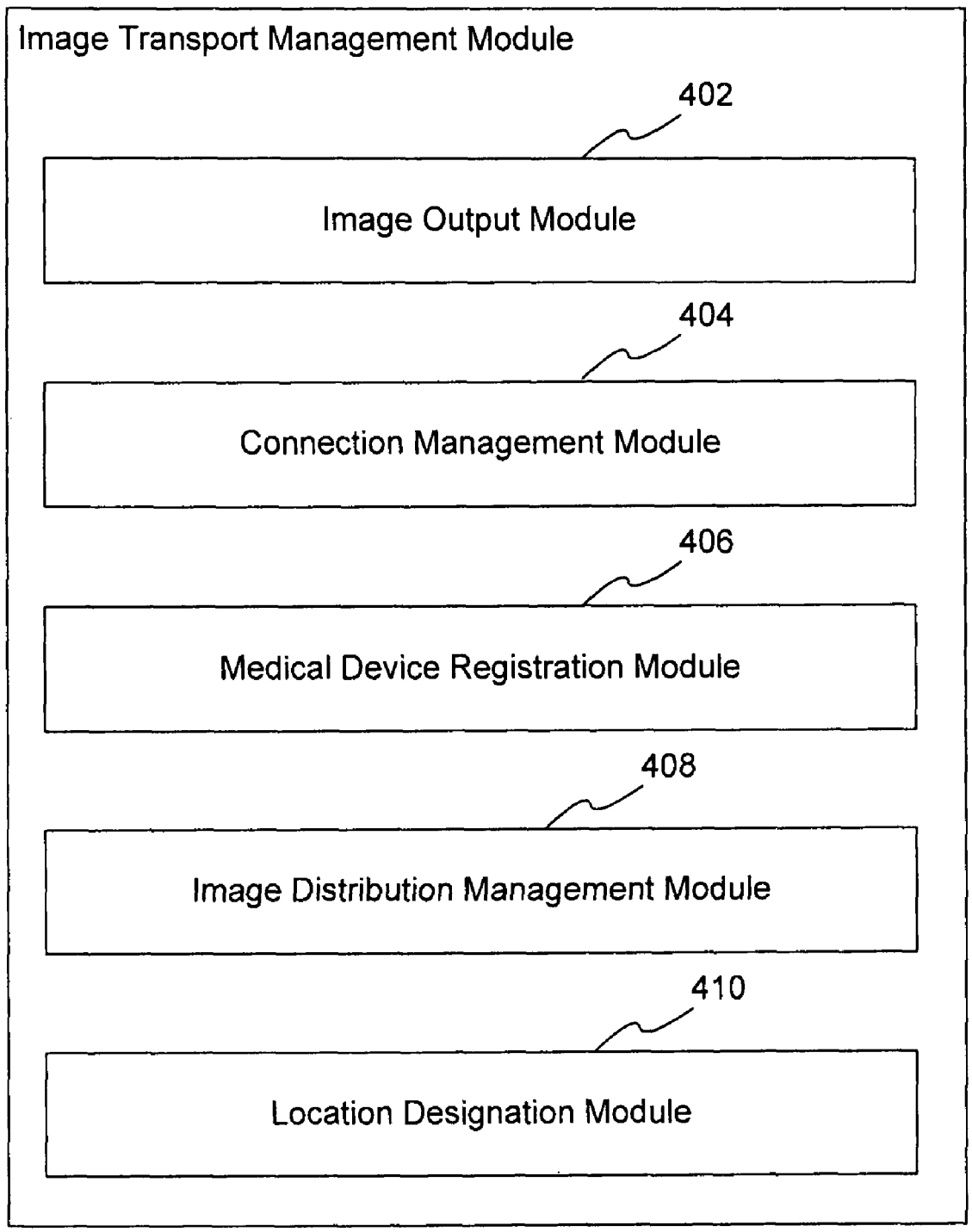
FIG. 4 is a block diagram illustrating an embodiment of an image transport management module.

FIG. 4 is a block diagram illustrating an embodiment of an image transport management module 400. Although one modularization is indicated, it should be understood that the image transport functionality may be provided using greater, fewer, or differently named modules. The image transport management module 400 includes an image output module 402, a connection management module 404, a medical device registration module 406, an image distribution management module 408, and a location designation module 410.

The image output module 402 maintains information regarding the types of devices to which images are transported as well as the corresponding formats for those images. In many examples, the images will be retained and transported using compressed formats, but in others raw digital image data may be required. The image output module 402 associates recipient devices or particular recipients to these requirements, such as in a table or other database that identifies such information.

The connection management module 404 manages and communicates with other PMID elements to instruct them to carry out the various types of connections required or desired for communications with other devices, including but not limited to connection to other devices through the wireless LAN. The connection management module 404 is also in communication with the image output module 402 to relay instructions corresponding to a desired image output in carrying out the connection and communications with the recipient device.

The medical device registration module 406 maintains and updates the database of information about devices with which the PMID may communicate to send and receive medical images. In one example, the device is a medical device having an image capture capability. This allows the PMID to receive images captured from that device, in lieu of using the image capture functionality provided by the PMID. Devices may also include other devices, including but not limited to other PMIDs, printers, displays, etc. The registration module 406 uniquely identifies each device and also preferably stores other information about the device, including default format, format capabilities, default display mode, display capabilities, and location. The other information about the device also preferably includes device classification, a list of one or more individuals associated with the device, and other information useful for carrying out restricted transport modes of operation. The database referred to for the medical device registration module 406 may be separate from that of the image output module 402 or, more preferably, the various modules may correspond with a single database of information managed by the image transport management module 400.

The image distribution management module 408 manages the transport of images including an identification of characteristics related to an image to be transported as well as the information about recipients and recipient devices. In that regard, the image distribution management module 408 accommodates receipt of input from the user wherein the user indicates which devices or individuals are to receive images, and which devices are to provide images to the PMID. This may be accommodated by the graphical user interface provided through the PMID display and corresponding input from the control buttons. In this regard, the image distribution management module 408 accesses and augments the information in the image transport management module 400 database.

The image distribution management module 408 also carries out transport restrictions. In one mode of operation, the transport of images is not subject to restrictions. There, the image distribution management module 408 communicates with the medical device registration module 406 and the image output module 408, ensures that an image can be sent (e.g., format compatibility, etc.), and interfaces with the user to resolve any incompatibility or other issues that arise in connection with a requested image transport. When there are restrictions on image transport, the image distribution management module 408 still performs the above processes, but also subjects any requested image transport to the restrictions that are identified in association with the particular image, location, originating device, destination device, etc. For example, the event of image capture may correspond to a particular procedure that is performed on a particular patient. A patient code identifies the record for this image and allows correlation to other information fields including the identification of the procedure, the patient's consent (level, designated authorized recipient, etc.) for image transport, etc.

The location designation module 410 allows designations of various locations that are stored and maintained, in correlation with functionality that is dictated or initiated by the location of the PMID. In one embodiment, the PMID includes location determining technology such as GPS, which allows ascertaining the location of the PMID at any given time. In conjunction with this, the location designation module 410 may store coordinates corresponding to local areas of interest. For example, the coordinates of a particular operating room may be identified. When the PMID is determined to be present within a given radius from those coordinates, it is determined that the PMID is present in that particular operating room. This location designation may also be correlated to which patient is in the room (with correlation to time using a trusted clock either resident in the PMID or communicated to the PMID being available to further this determination as well), which medical devices are presumed to be in the operating room, as well as doctors, other medical personnel, etc.

In another example, a specific signal is provided in areas of interest, with the PMID receiving the beacon signal and distinguishing particular locations accordingly. The specific signal may, for example, be a short range wireless communication that also embeds an identification code corresponding to the location (e.g., operating room 1, scanning room 1, operating room 2, etc.). The location is thus identified to the PMID. The ordinarily skilled artisan will readily recognize other alternatives for conveying the location of the PMID and associating it with particular locations.

As another example, the PMID is used for patient monitoring and reporting, preferably with the PMID communicating wirelessly with other medical products (e.g., heart monitoring, blood pressure, etc.). In this example, a medical practitioner could be altered of a sudden change in the patient's vital signs. In addition this alert could be captured on the imaging device as an additional recorded event. The medical practitioner (e.g., a doctor) could upon receipt of such an alert choose to mute the audible alert and have the display show vital status, update information or other information about the medical condition. Additionally, a simple text message from another medical device could be sent to the PMID. In that circumstance, the doctor would be able to read this on the spot and update this information to an existing electronic medical record.

Doctors would be able to easily view on the PMID display screen if there were any alerts for his patients, saving time and keeping informed without having to call a nurse or another attending physician oh a patient's status.

As an additional example, real time monitoring is provided where the associated medical device transmits an electronic signal back to an intensive care monitoring station. This image transporter could connect to an already existing system within the hospital network.

With regard to medical environments, the PMID can be used in all areas of a hospital or stand alone imaging center or private practice. Any medical device or medical system that can capture images, provide detailed scientific medical information can be interfaced with the PMID. Examples include but are not necessarily limited to:

Ultrasound-systems from GE, Siemens, Philips, Aloka B&K Medical, Biosound Easote;
PET/CT Scanners;
Surgical Cameras;
Surgical Lights with built in cameras;
Endoscopic Systems—from Olympus, Karl Storz, Stryker, Smith& Nephew, Pentax, Fujinon, Conmed, Linvatec, etc.;
X-RAY systems;
Direct X-ray systems (Canon, Kodak);
CR Systems-Computerized Radiography;
DR-Direct Radiography;
Film Imagers;
Printers;
Surgical Capture Boxes;
DICOM Networks;
Video Conferencing Systems;
Microscopy capture systems;
Dental Imaging Devices, including digital x-ray, panoramic digital systems; and
Opthamolic refraction systems that can capture images.

Figure 5:
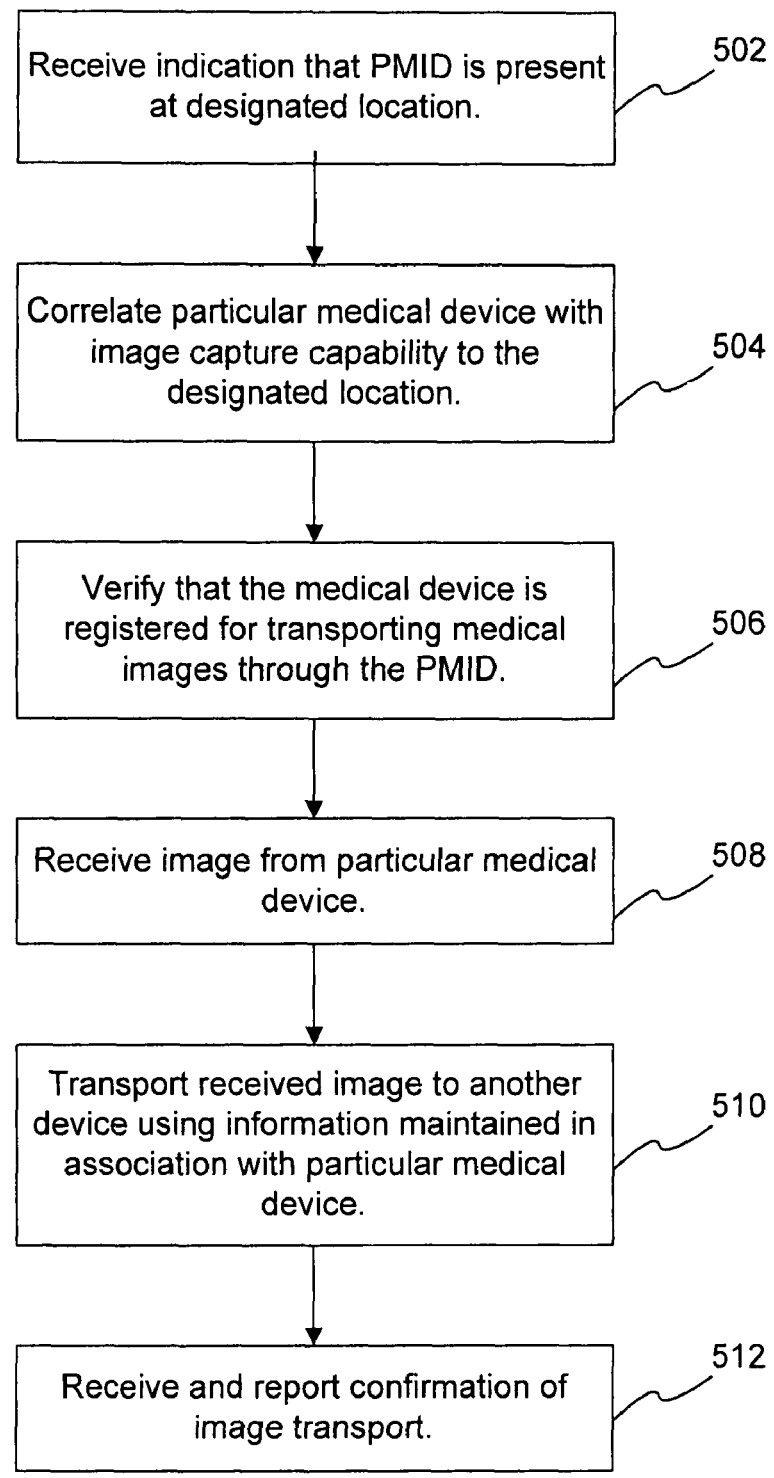
FIG. 5 is flow diagram illustrating an embodiment of a process for digital image transport that includes automatic activation and medical device recognition.

FIG. 5 is flow diagram illustrating an embodiment of a process 500 for digital image transport that includes automatic activation and medical device recognition, which includes receiving 502 indication that the PMID is present at a designation location. As noted, this may be by a specific signal that includes information identifying a location, using GPS or similar technology to recognize that the PMID is located at a particular location through comparison to previously input coordinates for that particular location, or other mechanisms.

The PMID also correlates 504 the particular medical device with the designated location. To do this, the PMID retains information including an identification of one or more medical devices that are associated with the designated location. The medical devices have image capture capability and are configured to communicate wirelessly. This allows the PMID to engage in initial communications and to identify that the particular medical device is active in the designated location. In conjunction with correlation of the designated location to the medical-device, the PMID also verifies 506 that the medical device is registered for transporting medical images through the PMID, again by making reference to the database of information. There may or may not be restrictions on such transport.

Once these initialization procedures have taken place, the PMID may receive 508 one or more images from the particular medical device. These images may then be transported 510 as requested by the user. For example, the user may want to print the image on a printer within the designated location. This may be actuated by the noted control buttons in conjunction with the user interface provided by the PMID display screen. Additional transport options have been described previously, and may include distribution of the image to other devices at the same or other locations. The PMID retains format and other information regarding the captured image as well as the demands of recipient devices, and thus may indicate compatibility issues or adjust accordingly (e.g., encoding to a different format prior to sending to another device).

The PMID may also be equipped with encryption capability should secure communication be sought, in addition to whatever security techniques are applied to the wireless communication channel between devices. Finally, the PMID is equipped to receive and report 512 confirmation of successful image transport, such as by an indication that the image has been sent or that the image has been printed.

Figure 6:
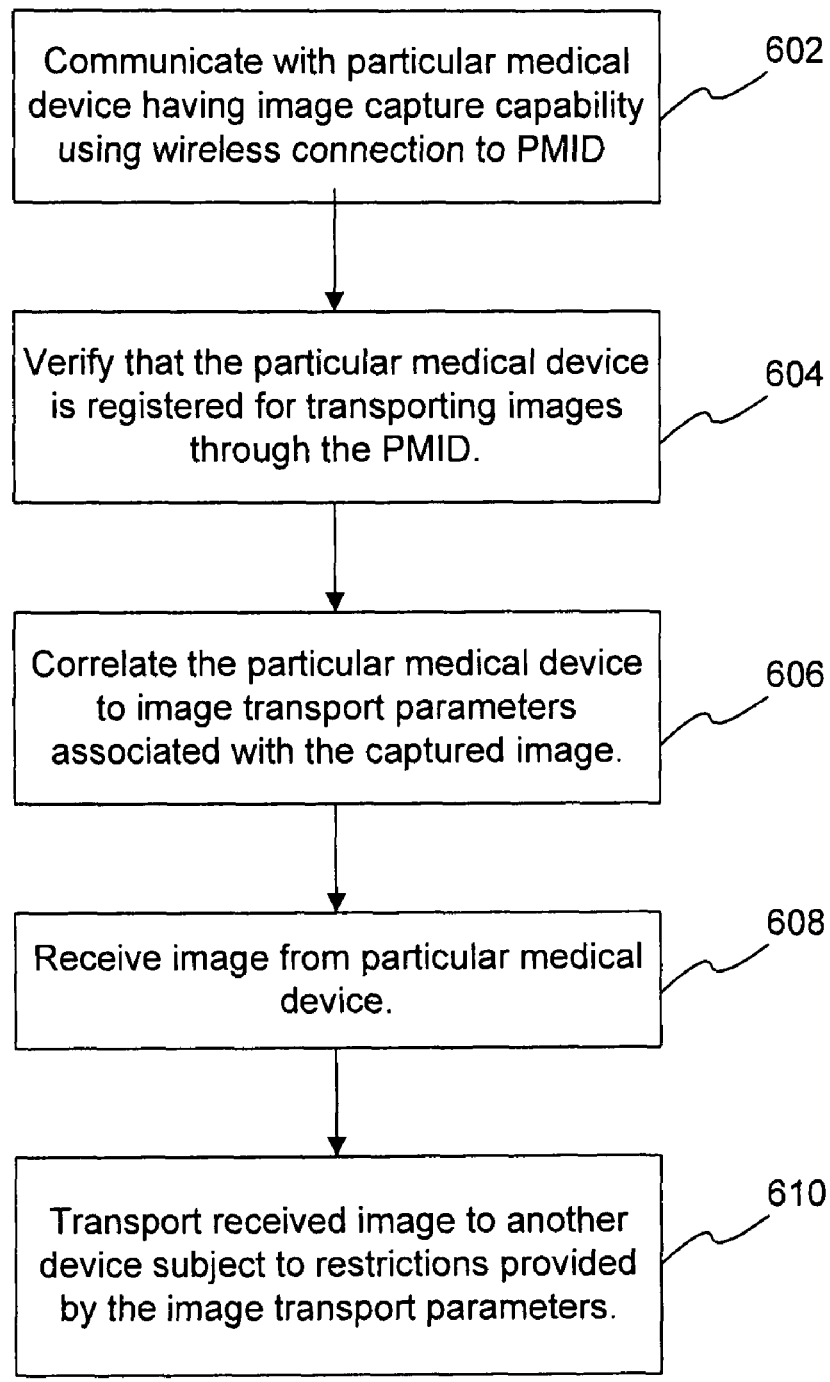
FIG. 6 is a flow diagram illustrating an embodiment of a process for digital image transport that includes recognition and execution of restrictions regarding medical information.

FIG. 6 is a flow diagram illustrating an embodiment of a process 600 for digital image transport that includes recognition and execution of restrictions regarding medical information. As previously described, the PMID communicates 602 with one or more medical devices having image capture capability, preferably through the wireless connection, and it is verified 604 that the particular medical device in question is registered for transporting images through the PMID.

The PMID correlates 606 the particular medical device to image transport parameters that are associated with the captured image. As described above, this may be performed by referencing database information corresponding to the particular medical device, the corresponding procedure being performed, time of day, the identification of the patent, etc. It should be noted that the PMID does not necessarily need to completely rely upon self-stored or maintained information to make the correlation to the image transport parameters. When connected to a medical information management system, for example, the PMID may simply access the image transport parameters for a given procedure from that system. As also described previously, the image transport parameters may include information about the image itself, such as preferred formats and other destination display constraints. The image transport parameters also include designations as to particular devices, particular individuals, or classes of devices or individuals that may receive or otherwise access the captured image. Accordingly, the PMID receives 608 the image from the particular image device, and then transports 610 the received image to another device subject to restrictions provided by the image transport parameters.

It is noted that although medical image capture and transport is one example of a useful application, the imaging device of the present invention is not limited to such applications. For example, the device may be used in broadcast video applications, video conferencing, and other applications.

With regard to broadcast video, the device may select MPEG-2 clips from XDCAM, whether SD or HD, sent to the device for viewing or sharing. Images may also be transmitted to an HD Exchange network system for sharing files and archiving in a broadcast environment. With regard to video conferencing, the device may implement two way audio and video.

The device can also be used to send video clips (containing images and/or video) to a monitor equipped with an IP expansion port. This allows anyone using the device to share movie clips, audio clips, still images, etc. with others on a larger screen.

Thus embodiments of the present invention produce and provide methods and apparatus for image transport. Although the present invention has been described in considerable detail with reference to certain embodiments thereof, the invention may be variously embodied without departing from the spirit or scope of the invention. Therefore, the following claims should not be limited to the description of the embodiments contained herein in any way.

The invention claimed is:

1. A method for transporting medical images through a portable medical image device that receives and transports medical images, the method comprising:

receiving an indication that the portable medical image device is present at a designated location;
communicating with a medical device having an image capture capability upon receiving the indication that the portable medical image device is present at the designated location;
verifying that the medical device is registered for transporting images through the portable medical image device;
receiving an image from the medical device; and
transporting the received image to an other device,
wherein the medical device at a given time is associated with a patient, and wherein image transport parameters incorporate identification of the patient in association with recipient classification information to restrict distribution of the images accordingly.

2. The method of claim 1, wherein transporting the received image is to a printer through a wireless connection, and a confirmation of successful printing is returned to the portable medical image device using the wireless connection while it is at the designated location.

3. The method of claim 1, further comprising:
correlating the medical device to information comprising image transport parameters that define restrictions in transporting images using the registered medical device.

4. The method of claim 1, wherein transporting the received image to the other device is performed using a wireless connection.

5. The method of claim 4, wherein the wireless connection is a wireless LAN connection.

6. The method of claim 1, wherein an audio annotation is associated to the received image prior to transporting the received image.

7. An apparatus for transporting medical images through a portable medical image device that receives and transports medical images, the apparatus comprising:
means for receiving an indication that the portable medical image device is present at a designated location;
means for communicating with a medical device having an image capture capability upon receiving the indication that the portable medical image device is present at the designated location;
means for verifying that the medical device is registered for transporting images through the portable medical image device;
means for receiving an image from the medical device; and
means for transporting the received image to an other device, wherein the medical device at a given time is associated with a patient, and wherein image transport parameters incorporate identification of the patient in association with recipient classification information to restrict distribution of the images accordingly.

8. The apparatus of claim 7, wherein transporting the received image is to a printer through a wireless connection, and a confirmation of successful printing is returned to the portable medical image device using the wireless connection while it is at the designated location.

9. The apparatus of claim 7, wherein transporting the received image to the other device is performed using a wireless connection.

10. The apparatus of claim 9, wherein the wireless connection is a wireless LAN connection.

11. The apparatus of claim 7, wherein an audio annotation is associated to the received image prior to transporting the received image.

12. An apparatus for transporting medical images through a portable medical image device that receives and transports medical images, the apparatus comprising:
a location designation module, which receives an indication that the portable medical image device is present at a designated location;
a connection management module, which communicates with a medical device having an image capture capability upon receiving the indication that the portable medical image device is present at the designated location;
a medical device registration module, which verifies that the medical device is registered for transporting images through the portable medical image device; and
an interface, which receives an image from the medical device, and transports the received image to an other device,
wherein the medical device at a given time is associated with a patient, and wherein image transport parameters incorporate identification of the patient in association with recipient classification information to restrict distribution of the images accordingly.

13. The apparatus of claim 12, wherein transporting the received image is to a printer through a wireless connection, and a confirmation of successful printing is returned to the portable medical image device using the wireless connection while it is at the designated location.

14. The apparatus of claim 12, wherein transporting the received image to the other device is performed using a wireless connection.

15. The apparatus of claim 12, wherein an audio annotation is associated to the received image prior to transporting the received image.

16. A method for transporting images through a portable image device that receives and transports images, the method comprising:
communicating with a medical device having an image capture capability using a wireless connection between the portable image device and the device;
verifying that the medical device is registered for transporting images through the portable image device;
correlating the medical device to information comprising image transport parameters that define restrictions in transporting images using the registered medical device;
receiving an image from the medical device; and
transporting the received image to an other device subject to restrictions provided by the image transport parameters,
wherein the medical device at a given time is associated with a patient, and wherein the image transport parameters incorporate identification of the patient in association with recipient classification information to restrict distribution of the images accordingly.

* * * * *